US011593936B2

(12) United States Patent
Patil et al.

(10) Patent No.: US 11,593,936 B2
(45) Date of Patent: Feb. 28, 2023

(54) ULTRASOUND IMAGING SYSTEM AND METHOD FOR PROVIDING FEEDBACK REGARDING ACQUISITION QUALITY

(71) Applicant: GE Precision Healthcare LLC, Wauwatosa, WI (US)

(72) Inventors: Rohan Keshav Patil, Bangalore (IN); Vikram Melapudi, Bangalore (IN); Prasad Sudhakara Murthy, Bangalore (IN); Christian Perrey, Mondsee (AT); Pavan Annangi, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 317 days.

(21) Appl. No.: 17/135,713

(22) Filed: Dec. 28, 2020

(65) Prior Publication Data
US 2022/0207717 A1 Jun. 30, 2022

(51) Int. Cl.
G06T 7/00 (2017.01)
G06T 7/10 (2017.01)
(Continued)

(52) U.S. Cl.
CPC .......... *G06T 7/0012* (2013.01); *A61B 8/0883* (2013.01); *A61B 8/463* (2013.01);
(Continued)

(58) Field of Classification Search
CPC ................ G06T 7/0012; G06T 7/10; G06T 2207/10132; G06T 2207/20084;
(Continued)

(56) References Cited

U.S. PATENT DOCUMENTS 9,734,626 B2 8/2017 Jago
2002/0072671 A1* 6/2002 Chenal ...................... G06T 7/12
600/450
(Continued)

FOREIGN PATENT DOCUMENTS

WO WO-0245586 A1 * 6/2002 ............ A61B 8/065
WO WO-2005030057 A1 * 4/2005 ........... A61B 5/1075
(Continued)

OTHER PUBLICATIONS

Arnaout et al., "Deep-learning models improve on community-level diagnosis for common congenital heart disease lesions," Subjects: Computer Vision and Pattern Recognition, arXiv:1809.06993 [cs.CV], [v1], Sep. 19, 2018, 17 pages.
(Continued)

Primary Examiner — Shefali D Goradia

(57) ABSTRACT

A method and ultrasound imaging system includes generating a cine including a plurality of cardiac views based on the cardiac ultrasound data, segmenting a plurality of cardiac chambers from each of the plurality of cardiac images, and automatically determining a cardiac chamber area for each of the plurality of cardiac chambers. The method and ultrasound imaging system includes displaying the cine on a display device and displaying a plurality of single trace curves on the display device at the same time as the cine to provide feedback regarding an acquisition quality of the cine, wherein each of the single trace curves represents the cardiac chamber area for a different one of the plurality of cardiac chambers over the plurality of cardiac cycles.

20 Claims, 7 Drawing Sheets

(51) Int. Cl.
*A61B 8/08* (2006.01)
*A61B 8/00* (2006.01)

(52) U.S. Cl.
CPC ............... *A61B 8/467* (2013.01); *A61B 8/54* (2013.01); *G06T 7/10* (2017.01); *G06T 2207/10132* (2013.01); *G06T 2207/20084* (2013.01); *G06T 2207/30048* (2013.01); *G06T 2207/30168* (2013.01)

(58) Field of Classification Search
CPC . G06T 2207/30048; G06T 2207/30168; A61B 8/0883; A61B 8/463; A61B 8/467; A61B 8/54
See application file for complete search history.

(56) References Cited

U.S. PATENT DOCUMENTS

| | | | |
|---|---|---|---|
| 2010/0168578 A1* | 7/2010 | Garson, Jr. | A61B 8/0858 600/509 |
| 2016/0081662 A1* | 3/2016 | Denk | A61B 8/54 600/437 |
| 2020/0064469 A1* | 2/2020 | Trahey | G06N 20/00 |

FOREIGN PATENT DOCUMENTS

| | | | | |
|---|---|---|---|---|
| WO | WO-2005096226 A2 * | 10/2005 | ........... | G06T 7/0012 |
| WO | WO-2020162989 A1 * | 8/2020 | ........... | A61B 8/4254 |

OTHER PUBLICATIONS

Bridge et al., "Automated annotation and quantitative description of ultrasound videos of the fetal heart," Med Image Anal. Feb. 2017; 36:147-161. doi: 10.1016/j.media.2016.11.006. Epub Nov. 19, 2016, 15 pages.

Carvalho et al., "ISUOG Practice Guidelines (updated): sonographic screening examination of the fetal heart" Ultrasound Obstet Gynecol 2013; 41: 348-359, wileyonlinelibrary.com. DOI: 10.1002/uog.12403.

Dezaki et al., "Cardiac Phase Detection in Echocardiograms With Densely Gated Recurrent Neural Networks and Global Extrema Loss," in IEEE Transactions on Medical Imaging, vol. 38, No. 8, pp. 1821-1832, Aug. 2019, doi: 10.1109/TMI.2018.2888807, 12 pages.

Smistad et al., "Fully Automatic Real-Time Ejection Fraction and MAPSE Measurements in 2D Echocardiography Using Deep Neural Networks," 2018 IEEE International Ultrasonics Symposium (IUS), Kobe, 2018, pp. 1-4, doi: 10.1109/ULTSYM.2018.8579886, 4 pages.

Xu et al., "Convolutional-Neural-Network-Based Approach for Segmentation of Apical Four-Chamber View from Fetal Echocardiography," in IEEE Access, vol. 8, pp. 80437-80446, 2020, doi: 10.1109/ACCESS.2020.2984630, 10 pages.

Yu et al., "Segmentation of Fetal Left Ventricle in Echocardiographic Sequences Based on Dynamic Convolutional Neural Networks," in IEEE Transactions on Biomedical Engineering, vol. 64, No. 8, pp. 1886-1895, Aug. 2017, doi: 10.1109/TBME.2016.2628401, 10 pages.

* cited by examiner

ULTRASOUND IMAGING SYSTEM AND METHOD FOR PROVIDING FEEDBACK REGARDING ACQUISITION QUALITY

FIELD

Embodiments of the subject matter disclosed herein relate to a method and system of ultrasound imaging, and more particularly to displaying a plurality of single traces over a plurality of cycles at the same time as a cine in order to provide feedback regarding an acquisition quality of the cine.

BACKGROUND

In ultrasound imaging, it is oftentimes desirable to obtain a 4-chamber view of a patient's heart. It is important to acquire and identify a plurality of cardiac images of the desired view before performing any type of assessment or measurements based on the cardiac images. Identifying a plurality of cardiac images of the 4-chamber view with a high acquisition quality can be challenging for some clinicians.

For example, the 4-chamber view is commonly acquired during both adult and fetal ultrasound scan protocols. A high-quality 4-chamber view depicts the left ventricle, the right ventricle, a left atrium, and a right atrium. The 4-chamber view is commonly used for performing routine measurements on the patient's heart. These measurements may be used to make cardiac assessments for that patient and/or to help screen for potential abnormalities and defects. For example, the 4-chamber view may be used to detect congenital cardiac anomalies such as septal defects, hypoplastic left heart syndrome, persistent truncus arteriosus, or the presence of echogenic intracardiac foci.

A high-quality 4-chamber view should clearly show all four chambers of the heart: the left ventricle, the right ventricle, a left atrium, and a right atrium. The septum should be positioned in a generally vertical position in a high-quality 4-chamber view. The plane of the 4-chamber view should ideally pass through the apex of the patient's heart. If the plane does not pass through the apex, the resulting view will be foreshortened, which may make it difficult or impossible to make some or all of the desired measurements in order to make a definitive cardiac assessment.

In many ultrasound procedures, the sonographer is viewing images during the process of scanning in real-time. The sonographer may adjust the position and/or orientation of the ultrasound probe and see the resulting changes of the adjusted position/orientation of the ultrasound probe based on how the real-time image is updated. It can be difficult for a sonographer to properly obtain images with a high acquisition quality of the desired cardiac view in real-time or based on saved ultrasound data. As such, there is a need for an improved method and ultrasound imaging system for providing feedback regarding the acquisition quality of cardiac ultrasound images with respect to the 4-chamber view.

BRIEF DESCRIPTION

In one embodiment, a method of ultrasound imaging includes accessing with a processor cardiac ultrasound data, generating a cine based on the cardiac ultrasound data, wherein the cine includes a plurality of cardiac images acquired over a plurality of cardiac cycles. The method includes automatically segmenting a plurality of cardiac chambers from each of the plurality of cardiac images, automatically determining a cardiac chamber area for each of the plurality of cardiac chambers segmented from each of the plurality of cardiac images, and displaying the cine on a display device. The method includes displaying a plurality of single trace curves on the display device at the same time as the cine to provide feedback regarding an acquisition quality of the cine, wherein each of the plurality of single trace curves represents the cardiac chamber area for a different one of the plurality of cardiac chambers over the plurality of cardiac cycles. The method includes receiving a selection of a portion of the cine based on the information displayed in the plurality of single trace curves and saving the portion of the cine in a memory as a 4-chamber view based on the selection.

In one embodiment, an ultrasound imaging system includes an ultrasound probe, a user interface, a display device, and a processor in electronic communication with the ultrasound probe, the user interface and the display device. The processor is configured to control the ultrasound probe to acquire cardiac ultrasound data and generate a cine based on the cardiac ultrasound data, wherein the cine includes a plurality of cardiac images. The processor is configured to automatically segment a plurality of cardiac chambers from each of the plurality of cardiac images and automatically determine a cardiac chamber area for each of the plurality of cardiac chambers segmented from each of the plurality of cardiac images. The processor is configured to display the cine on the display device and display a plurality of single trace curves on the display device at the same time as the cine to provide feedback regarding an acquisition quality of the cine, wherein each of the plurality of single trace curves represents the cardiac chamber area for a different one of the plurality of cardiac chambers over the plurality of cardiac cycles. The processor is configured to receive a selection of a portion of the cine based on the information displayed in the plurality of single trace curves and save the portion of the cine in the memory as a 4-chamber view.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
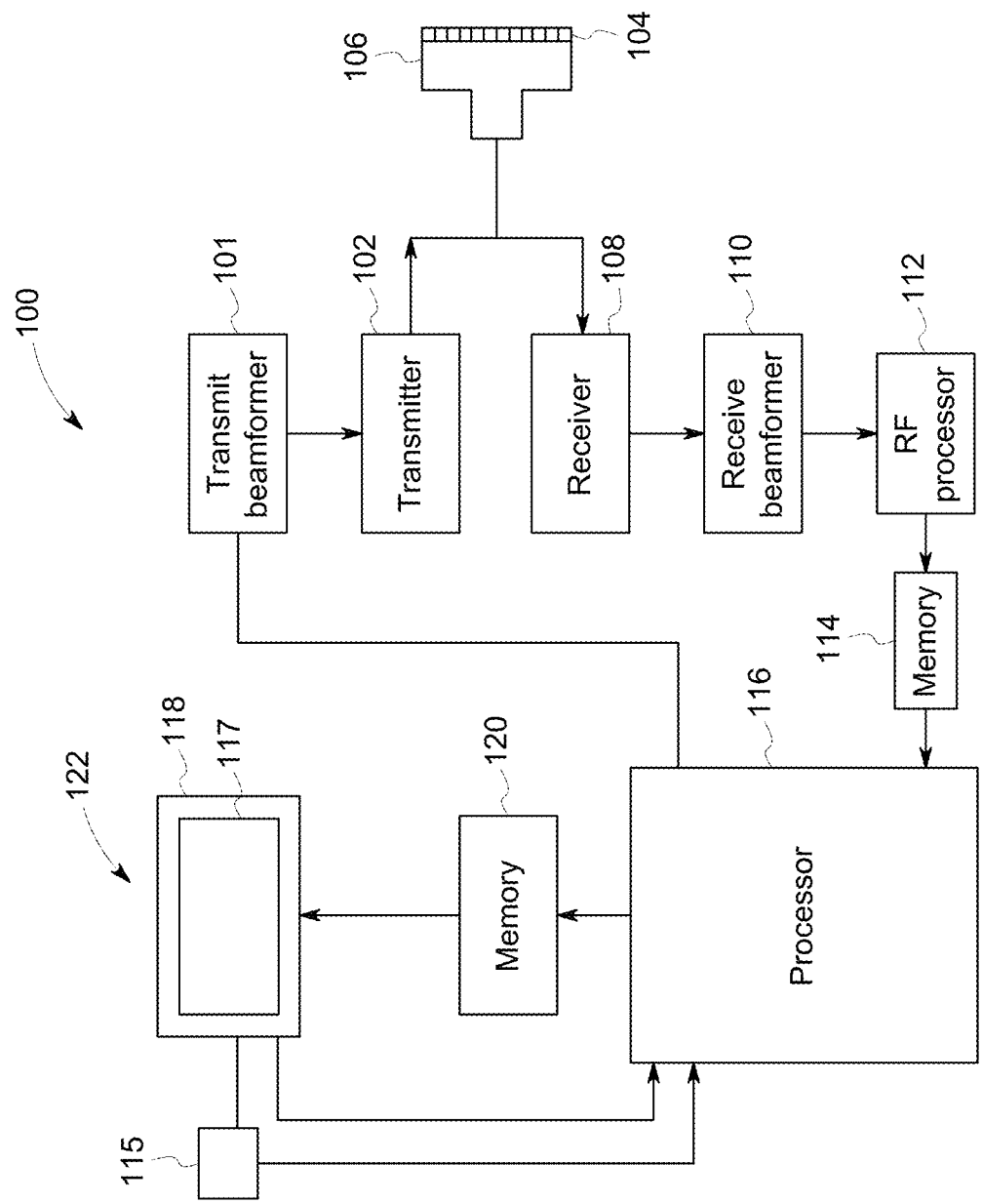
FIG. 1 shows a schematic representation of an ultrasound imaging system according to an exemplary embodiment.

FIG. 1 depicts a block diagram of an ultrasound imaging system 100 in accordance with an exemplary embodiment. Furthermore, it is understood that other embodiments do not actively acquire ultrasound data. Instead, embodiments may retrieve image or ultrasound data that was previously acquired by an ultrasound imaging system and analyze the image data as set forth herein. As shown, the ultrasound imaging system 100 includes multiple components. The components may be coupled to one another to form a single structure, may be separate but located within a common room, or may be remotely located with respect to one another. For example, one or more of the modules described herein may operate in a data server that has a distinct and remote location with respect to other components of the ultrasound imaging system 100, such as an ultrasound probe and user interface. The ultrasound imaging system 100 may be configured as a workstation; the ultrasound imaging system 100 may be a portable or hand-carried system, such as a laptop-style system, a table-based system, or a system with a form-factor similar to a smartphone; or the ultrasound imaging system 100 may be a cart-mounted system on a cart with wheels that is configured to be easily moved via the cart.

In the illustrated embodiment, the ultrasound imaging system 100 includes a transmit beamformer 101 and transmitter 102 that drives an array of elements 104, for example, piezoelectric crystals, within an ultrasound probe 106 (or transducer) to emit ultrasonic signals (e.g., continuous or pulsed) into a body or volume (not shown) of a subject. According to other embodiments, the ultrasound probe 106 may be a micromachined ultrasonic transducer (MUT) or a capacitive micromachined ultrasonic transducer (CMUT). The elements 104 and the ultrasound probe 106 may have a variety of geometries. The ultrasonic signals are backscattered from structures in a body to produce echoes that return to the elements 104. The echoes are received by a receiver 108. The received echoes are provided to a receive beamformer 110 that performs beamforming and outputs a radio frequency (RF) signal. The RF signal is then provided to an RF processor 112 that processes the RF signal. Alternatively, the RF processor 112 may include a complex demodulator (not shown) that demodulates the RF signal to form I/Q data pairs representative of the echo signals. The RF or I/Q signal data may then be provided directly to a memory 114 for storage (for example, temporary storage). The system 100 also includes a processor 116 that may be part of a single processing unit or distributed across multiple processing units. The processor 116 is configured to control operation of the system 100. The processor 116 may include a central processing unit (CPU), one or more microprocessors, a graphics processing unit (GPU), or other electronic components capable of processing inputted data according to specific logical instructions stored on a memory of the processor 116 or coupled with the processor 116. Optionally, the processor 116 may include and/or represent one or more hardware circuits or circuitry that include, are connected with, or that both include and are connected with one or more processors, controllers, and/or other hardware logic-based devices.

For example, the processor 116 may include an image-processing module that receives cardiac ultrasound data (e.g., ultrasound signals in the form of RF signal data or I/Q data pairs) and processes image data. For example, the image-processing module may process the cardiac ultrasound data to generate 2D cardiac images or ultrasound waveforms (e.g., continuous or pulse wave Doppler spectrum or waveforms) for displaying to the operator. Similarly, the image-processing module may process the ultrasound signals to generate 3D renderings based on the cardiac ultrasound data. The image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography.

Acquired cardiac ultrasound data may be processed in real-time during an imaging session (or scanning session) as the echo signals are received. Additionally or alternatively, the ultrasound data may be stored temporarily in the memory 114 during an imaging session and processed in less than real-time in a live or off-line operation. A memory 120 is included for storing processed slices or waveforms of acquired ultrasound information that are not scheduled to be displayed immediately. The image memory 120 may comprise any known data storage medium, for example, a permanent storage medium, removable storage medium, and the like. Additionally, the image memory 120 may be a non-transitory storage medium.

In operation, an ultrasound imaging system 100 may acquire cardiac ultrasound data by various techniques (for example, 3D scanning, real-time 3D imaging, volume scanning, 2D scanning with probes having positioning sensors, freehand scanning using a voxel correlation technique, scanning using 2D or matrix array probes, and the like). Ultrasound spectrum (e.g., waveforms) and/or images may be generated from the acquired cardiac ultrasound data (at the processor 116) and displayed to the operator or user on the display device 118.

The processor 116 is operably connected to a user interface 122 that enables an operator to control at least some of the operations of the ultrasound imaging system 100. The user interface 122 may include hardware, firmware, software, or a combination thereof that enables an individual (e.g., an operator) to directly or indirectly control operation of the ultrasound imaging system 100 and the various components thereof. As shown, the user interface 122 includes a display device 118 having a display area 117. In some embodiments, the user interface 122 may also include one or more user interface input devices 115, such as a physical keyboard, mouse, touchpad, one or more sliders, one or more rotary controls, a trackball, or other control input devices. In one embodiment, a touchpad may be configured to the system processor 116 and display area 117, such that when a user moves a finger/glove/stylus across the face of the touchpad, a cursor atop the ultrasound image or Doppler spectrum on the display device 118 moves in a corresponding manner.

In an exemplary embodiment, the display device 118 may be a touch-sensitive display (e.g., touchscreen) that can detect a presence of a touch from the operator on the display area 117 and can also identify a location of the touch in the display area 117. The touch may be applied by, for example, at least one of an individual's hand, glove, stylus, or the like. As such, the touch-sensitive display may also be characterized as an input device that is configured to receive inputs from the operator (such as a request to adjust or update an orientation of a displayed image). The display device 118 also communicates information from the processor 116 to the operator by displaying the information to the operator. The display device 118 is configured to present information to the operator during or after the imaging or data acquiring session. The information presented may include ultrasound images (e.g., one or more 2D images and/or volumetric renderings), graphical elements, measurement graphics of the displayed images, user-selectable elements, user settings, and other information (e.g., administrative information, personal information of the patient, and the like). In other embodiments, the display device 118 may be a display that is not touch-sensitive.

In addition to the image-processing module, the processor 116 may also include one or more of a graphics module, an initialization module, a tracking module, and an analysis module. The image-processing module, the graphics module, the initialization module, the tracking module, and/or the analysis module may coordinate with one another to present information to the operator during and/or after the imaging session. For example, the image-processing module may be configured to display an acquired image on the display device 118, and the graphics module may be configured to display designated graphics along with the displayed image, such as selectable icons (e.g., image rotation icons) and measurement parameters (e.g., data) relating to the image. The processor 116 may include algorithms and one or more neural networks (e.g., a system of neural networks) stored within a memory of the processor 116 for automatically recognizing a plurality of structures from each of a plurality of cardiac images. In some examples, the processor 116 may include a deep learning module which includes the one or more deep neural networks and instructions for performing the deep learning and feature recognition discussed herein.

The screen of a display area 117 of the display device 118 is made up of a series of pixels which display the data acquired with the ultrasound probe 106. The acquired data includes one or more imaging parameters calculated for each pixel, or group of pixels (for example, a group of pixels assigned the same parameter value), of the display, where the one or more calculated image parameters includes one or more of an intensity, velocity (e.g., blood flow velocity), color flow velocity, texture, graininess, contractility, deformation, and rate of deformation value. The series of pixels then make up the displayed image and/or Doppler spectrum generated from the acquired ultrasound data.

The acquired cardiac ultrasound data may be used to generate one or more cardiac ultrasound images which may then be displayed via the display device 118 of the user interface 115. The one or more generated cardiac ultrasound images may include a 2D image and/or a volumetric rendering based on 3D ultrasound data, for example. For example, the image-processing module discussed above may be programmed to generate and simultaneously display the 2D image slice and the 3D rendering.

Figure 2:
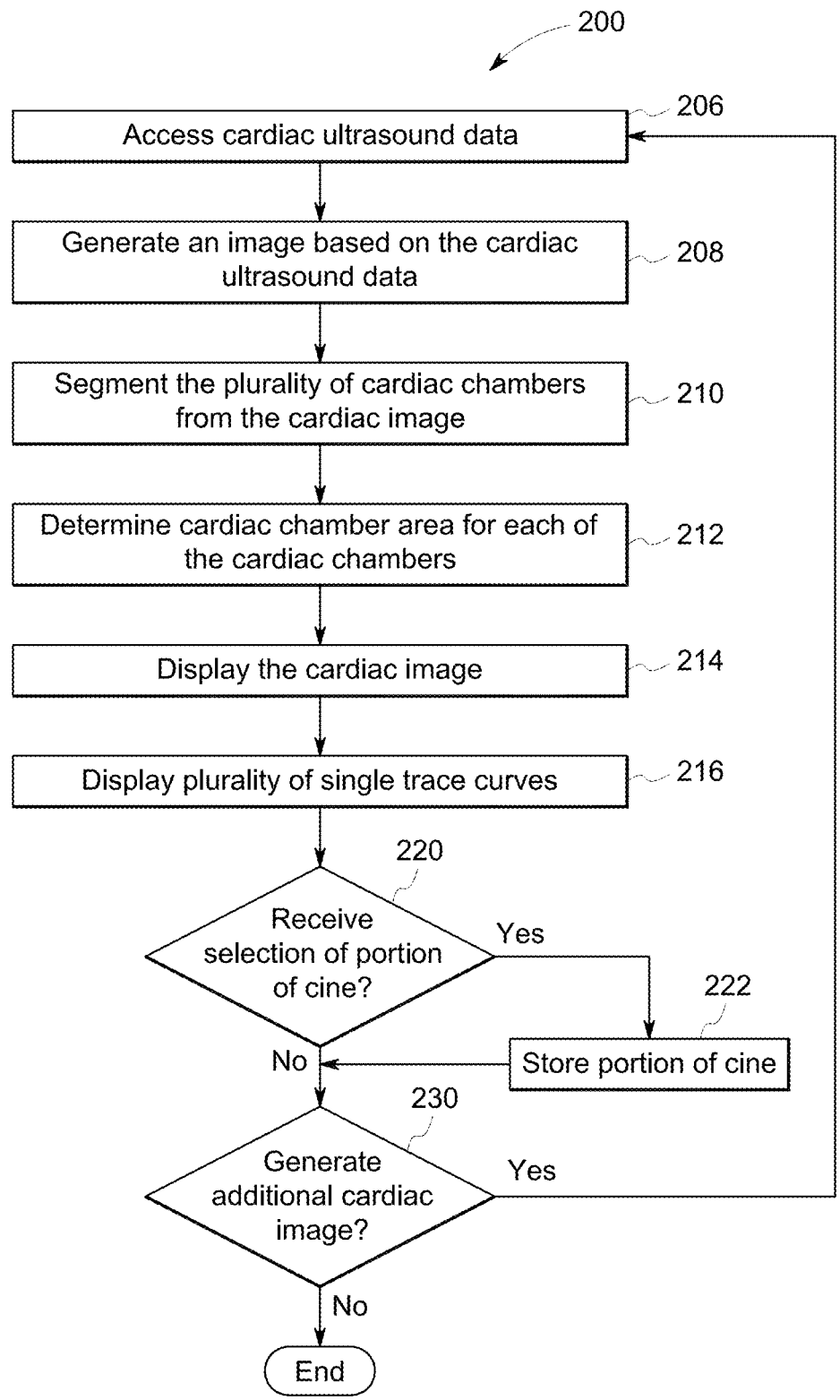
FIG. 2 shows a flow chart of a method according to an embodiment.

FIG. 2 is a flow chart of a method in accordance with an exemplary embodiment. The technical effect of the method 200 is the display of a cine including a plurality of cardiac images and a plurality of single trace curves on a display device at the same time. Each of the plurality of single trace curves represents a cardiac chamber area over a plurality of cardiac cycles. The display of the plurality of single trace curves at the same time as the cine provides feedback regarding an acquisition quality of the cine.

Figure 3:
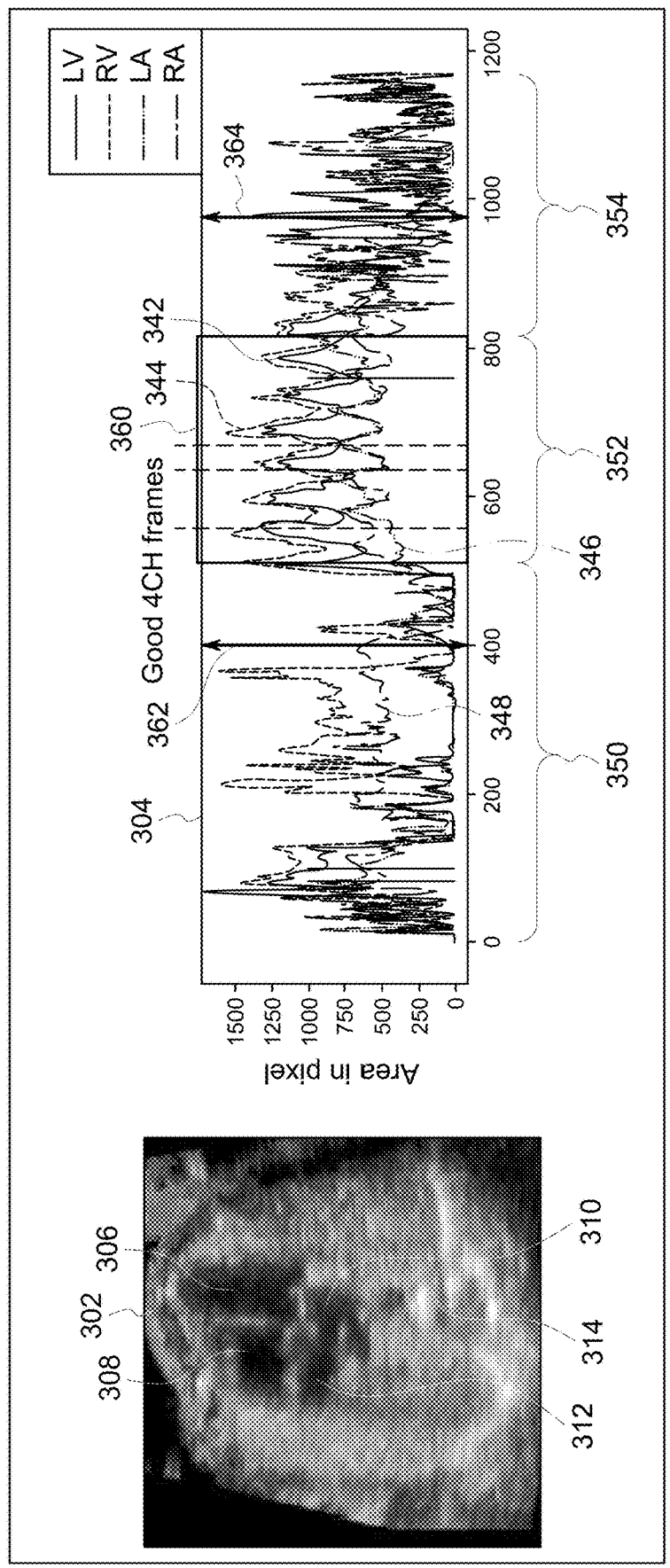
FIG. 3 shows a cardiac image and plurality of single trace curves according to an embodiment.

Referring now to FIG. 3, a cardiac image 302 and a plurality of single trace curves 304 are shown in accordance with an exemplary embodiment.

Method 200 is described below with regard to the ultrasound imaging system and components depicted in FIG. 1, though it should be appreciated that method 200 may be implemented with other ultrasound systems and components without departing from the scope of the present disclosure. In some embodiments, method 200 may be implemented as executable instructions in any appropriate combination of the ultrasound imaging system 100, an edge device (e.g., an external computing device) connected to the ultrasound imaging system 100, a cloud in communication with the ultrasound imaging system, and so on.

Referring to FIG. 2, at step 206, the processor 116 accesses cardiac ultrasound data. According to an exemplary embodiment, the processor 116 may access one frame of cardiac ultrasound data at step 206, but according to other embodiments, the processor 116 may access two or more frames of cardiac ultrasound data at step 206. The processor 116 may access the cardiac ultrasound data from a memory, such as the memory 120, according to an embodiment. The cardiac ultrasound data may, for example, be stored from a previous ultrasound exam. According to an embodiment, the processor 116 may access the cardiac ultrasound data from the ultrasound probe 106 or from the memory 120 in real-time as cardiac ultrasound data is acquired as part of an ultrasound imaging exam. Or according to an embodiment, the processor 116 may use deep learning, such as by applying a neural network or a deep neural network to identify one or more possible four chamber views from the cardiac ultrasound data. For example, the neural network or the deep neural network may be trained to identify frames of cardiac ultrasound data that are likely show a four chamber view including all four chambers of the patient's heart.

At step 208, the processor 116 generates an image based on the cardiac ultrasound data accessed during step 206. Generating the image may require processing the cardiac ultrasound data into a format for display through a process such as scan conversion. Scan conversion involves translating the cardiac ultrasound data from the geometry used during the acquisition into a geometry a different coordinate system that is more well-suited for display on the display device 118 such as the Cartesian coordinate system.

FIG. 3 is a representation of a cardiac image 302 and a plurality of single trace curves 304 in accordance with an exemplary embodiment. The cardiac image 302 is a 4-chamber view in accordance with an embodiment. At step 208, the processor may generate an image such as the cardiac image 302 shown in FIG. 3. A 4-chamber view, such as the cardiac image 302 ideally shows all four cardiac chambers. The cardiac image 302 includes a left ventricle 306, a right ventricle 308, a left atrium 310, and a right atrium 312. The cardiac image 302 also includes a spine 314.

At step 210 of the method 200, the processor 116 automatically segments a plurality of cardiac chambers from the cardiac image generated at step 208. According to an embodiment where the desired cardiac view is a 4-chamber view, the plurality of structures segmented by the processor 116 at step 210 may include the left ventricle 306, the right ventricle 308, the left atrium 310, and the right atrium 312 from the cardiac image 302.

The processor 116 may also optionally segment one or more additional structures, such as a spine, an aorta, an interventricular septum (IVS), or another structure that could be used as a landmark. According to one exemplary embodiment, the processor 116 may be configured to segment the plurality of cardiac chambers (i.e., the left ventricle 306, the right ventricle 308, the left atrium 310, and the right atrium 312) from the cardiac image 302. According to another exemplary embodiment, the processor 116 may be configured to segment the plurality of cardiac chambers (i.e., the left ventricle 306, the right ventricle 308, the left atrium 310, and the right atrium 312) and one or more other structures, such as a spine 314, from the image at step 210.

The processor 116 may be configured to identify the plurality of cardiac chambers for segmenting at step 210 using image processing techniques such as shape-based identification. The processor 116 may, for instance, use a model (either a rigid or a deformable model) or a template in order to identify the plurality of cardiac chambers. The processor 116 may be configured to operate in one or both of the image domain or the frequency domain through Fourier processing techniques in order to identify the plurality of cardiac chambers. According to other embodiments, the processor 116 may be configured to apply an artificial intelligence technique in order to segment the plurality of cardiac chambers representing landmarks from the image at step 210. For example, the processor 116 may be configured to apply a neural network, such as a deep neural network or a system of deep neural networks in order to identify and segment the plurality of cardiac chambers from the image 302. For example, in an exemplary embodiment, the processor 116 may apply a system of neural networks in order to segment the left ventricle 306, the right ventricle 308, the left atrium 310, and the right atrium 312 from the cardiac image 302. The neural network, or system of neural networks may for instance have been trained with a curated set of training images for the 4-chamber view. For example, the curated set of training images may include various images obtained from different patients with the plurality of cardiac chambers identified. The neural network or system of neural networks may then "learn" traits or characteristics identifying the cardiac chambers.

At step 212, the processor 116 is configured to determine a cardiac chamber area for each of the plurality of cardiac chambers in the cardiac image 302. The cardiac chamber areas are calculated/determined by the processor 116 based on the plurality of cardiac chambers segmented from the cardiac image 302. According to an embodiment, the cardiac chamber areas may be calculated in terms of pixels, as determined based on the cardiac chambers segmented during step 210. According to other embodiments, the processor 116 may calculate cardiac chamber areas in units of area such as $mm^2$ or $cm^2$.

At step 214, the processor 116 displays the cardiac image generated at step 208 on the display device 118. The cardiac image 302 may be displayed as part of a cine according to an embodiment.

At step 216, the processor 116 displays a plurality of single trace curves 304 on the display device 118 at the same time as the cardiac image 302. FIG. 3 includes a first single trace curve 342, a second single trace curve 344, a third single trace curve 346, and a fourth single trace curve 348. Additional details about the plurality of single trace curves will be discussed hereinafter.

At step 220, a selection of the portion of the cine is optionally received. At step 220, the processor 116 may optionally receive a selection indicating a portion of the cine for storage. The processor 116 may receive the selection of the portion of the cine either based on an input entered through the user interface or the processor 116 may automatically receive the selection of the portion of the cine. For example, the processor 116 may use or apply a neural network or a system of neural networks in order to identify the portion of a cine. According to an embodiment, the processor 116 may automatically identify the portion of the cine based on other automated techniques. Step 220 will be described in greater detail hereinafter.

If the processor 116 receives a selection of a portion of the cine at step 220, the method advances to step 222 where the portion of the cine is stored in the memory 120. According to an embodiment, the processor 116 may associate a tag identifying the portion of the cine as being representative of the 4-chamber view. After storing the portion of the cine at step 222, the method advances to step 230. If a selection of the portion of the cine is not received at step 220, the method advances to step 230.

At step 230, the processor 116 determines if it is desired to generate an additional cardiac image. If it is desired to generate an additional cardiac image, the method 400 returns to step 206. Steps 206, 208, 210, 212, 214, 216, 220 and 230 are iteratively repeated in order to display a cine image. It should be appreciated by those skilled in the art that if the selection of the portion of the cine is received at step 220, the method 200 will perform step 222 during that particular iteration as well.

The cine is refreshed each time a new cardiac image is generated and displayed based on a different frame of cardiac data during each iteration of performing steps 206, 208, 210, 212, 214, 216, 220 and 230. The plurality of single trace curves 304 is updated to include the cardiac chamber area for each of the cardiac chambers based on the current cardiac image of the cine. The processor 116 displays a cine on the display device 118 by displaying a plurality of cardiac images, where each of the cardiac images is based on cardiac ultrasound data acquired at a different time. Cine images are well-know by those skilled in the art and therefore will not be described in additional details. The cardiac image 302 shown on FIG. 3, for example, represents a cine at a single point in time. In the process of displaying the cine, the cardiac image 302 will be updated with an updated cardiac image each time the method iteratively performs steps 206, 208, 210, 212, 214, 216, 220 and 230. However, the plurality of single trace curves additionally includes historical plots of the cardiac chamber areas that were calculated or determined based the plurality of structures segmented from cardiac images acquired over one or more previous cardiac cycles.

Each of the plurality of single trace curves 304 represents a plot of the cardiac chamber area for one of the cardiac chambers plotted over time (i.e., the data for the each single trace curve is accumulated by repeating steps 206, 208, 210, 212, 214, 216, 220, and 230 multiple times to acquire cardiac chamber areas based on different frames of cardiac ultrasound data). According to the embodiment shown in FIG. 3, each of the plurality of single trace curves represents the cardiac chamber area associated with a different one of the plurality of cardiac chambers. The first single trace curve 342 represent the cardiac chamber area of the left ventricle 306 over a plurality of cardiac cycles, the second single trace curve 344 represents the cardiac chamber area of the right ventricle 308 over a plurality of cardiac cycles, the third single trace curve 346 represents the cardiac chamber area of the left atrium 310 over a plurality of cardiac cycles, and the fourth single trace curve 348 represents the cardiac chamber area of the right atrium 312 over a plurality of cardiac cycles. The plurality of single trace curves 304 are updated to include the cardiac chamber areas as calculated by the processor 116 based on the current cardiac image 302 in the cine, but they also include cardiac chamber areas calculated based on previous frames of data based on previous iterations of performing the steps 206, 208, 210, 212, 214, 216, 220, and 230.

In FIG. 3, the plurality of single trace curves 304 represents the cardiac chamber area for each of the plurality of chambers over a plurality of cardiac cycles. For example, the plurality of single trace curves 304 represent the cardiac chamber area for each of the plurality of chambers over more than three complete cardiac cycles according to the exemplary embodiment shown in FIG. 3. As the method 200 iteratively performs steps 206, 208, 210, 212, 214, 216, 220, and 230, the processor 116 determines the cardiac chamber area for additional cardiac images. According to an embodiment, the number of cardiac cycles represented in the plurality of single trace curves may increase as the method 200 iteratively performs steps 206, 208, 210, 212, 214, 216, 220, and 230 additional times. According to other embodiments, the plurality of single trace curves may display cardiac chamber areas over a predetermined number of cardiac cycles. The plurality of single trace curves 304 represents at least two cardiac cycles, but according to embodiments, the plurality of single trace curves 304 may show a different number of cardiac cycles. The plurality of single trace curves may be configured to show either an integral or a non-integral number of cardiac cycles greater than two according to various embodiments. The number of cardiac cycles represented in the plurality of single trace curves may be preset or it may be user adjustable via the user interface according to various embodiments.

The plurality of single trace curves 304 shown on FIG. 3 includes a first portion 350, a second portion 352, and a third portion 354. As described previously, the plurality of single trace curves 304 represents the cardiac chamber area for each of the cardiac chambers over time. In the first portion 350 and the third portion 354, the plurality of single trace curves do not exhibit a high amount of synchronization. In contrast, in the second portion 352, the plurality of single trace curves demonstrate a high amount of synchronization. In the second portion 352, the plurality of single trace curves (each single trace curves representing the cardiac chamber area of one of the four cardiac chambers) has a high amount of synchronization. In the second portion 352, there is a clearly defined periodicity to the single trace curves and period for each of the single trace curves is similar. Additionally, each of the single trace curves reaches local maxima or local minima at roughly similar times. In contrast, the single traces curves in the first portion 350 and the third portion 354 are not strongly synchronized. The periodicity of the plurality of single trace curves for the first portion 350 and the third portion 354 is much less pronounced than the periodicity of the second portion 352.

When a 4-chamber view is acquired with the ultrasound probe 106 in the correct location, the plurality of single trace curves 304, representing the cardiac areas over time, exhibit a high amount of synchronization. For example, the second portion 352 indicates a high amount of synchronization. The high amount of synchronization in the second portion 352 provides the clinician with qualitative feedback regarding the acquisition quality of the cine. The clinician can quickly and easily tell, by looking at the amount of synchronization exhibited by the plurality of single trace curves 304, the portion or portions of the cine that were acquired with the ultrasound probe 106 in the correct position and orientation to acquire a 4-chamber view with a high acquisition quality. According to an embodiment where the clinician is acquiring cardiac ultrasound data in real-time while viewing the cine and the plurality of single trace curves 304, the clinician may, for instance, adjust the position and/or the orientation of the ultrasound probe 106 using the plurality of single trace curves to provide feedback regarding the acquisition quality. The clinician may adjust the ultrasound probe 106 to a position and orientation where the plurality of single trace curves 304 have a high amount of synchronization, such as in the second portion 352. The plurality of single trace curves 304 may be used to provide real-time feedback to help the clinician position and orient the ultrasound probe 106 to acquire a 4-chamber view with high acquisition quality.

The processor 116 may display a graphical indicator 360 on the plurality of single trace curves 304 in order to indicate where the acquisition quality of the cine exceeds an acquisition quality threshold. The graphical indicator 360 surrounds the second portion 352 of the single trace curves, which is the portion where an acquisition quality, as determined by an amount of synchronization in the cardiac chamber areas, exceeds a threshold. Other embodiments may use a different type of graphical indicator in order to indicate where the acquisition quality exceeds a threshold. According to other embodiments, the graphical indicator may include a one or more lines, one or more brackets, color and/or highlighting in order to graphically show where the acquisition quality of the cine exceeds the acquisition quality threshold. The processor 116 may optionally use a neural network to determine where to position the graphical indicator 360 on the plurality of single trace curves 304. The processor 116 may adjust the positioning of the graphical indictor 360 in real-time as additional cardiac ultrasound data is represented in the plurality of single trace cures 304.

According to another embodiment, the clinician may be viewing cardiac ultrasound data that was acquired during a previous exam or scanning session. The clinician may use the plurality of single trace curves 304 in order to quickly and easily identify a portion of the cine with a high acquisition quality. For example, the clinician may use the plurality of single trace curves 304 as a guide to identify the portion of the cine with a high acquisition quality.

Referring to step 220 of the method 200, the clinician may select a portion of the cine for storage as a 4-chamber view using an input from the user interface. For example, the clinician may use the user interface to select the portion of the cine at step 220 that is saved at step 222. The clinician may select the portion of the cine by interacting with graphical user interface elements associated with the plurality of single trace curves 304. FIG. 3 shows graphical user interface elements according to an exemplary embodiment: FIG. 3 includes a first edge marker 362 and a second edge marker 364. The first edge marker 362 and the second edge marker 364 are graphical user interface elements that may be controlled by the clinician to select the portion of the cine through the user interface. The clinician may select a portion of the cine for storage based on an input entered through the user interface. According to an exemplary embodiment, the clinician may be able to control the position of first edge marker 362 and the second edge marker 364 in order to select the portion of the cine that corresponds to the portion of the plurality of single trace curves between the first edge marker 362 and the second edge marker 354. The user may, for example, position the first edge marker 362 at the left edge of the second portion 352 and position the second edge marker 364 at the right edge of the second portion 352 in order to select the a portion of the cine corresponding with the second portion 352 of the plurality of single trace curves 304. The user input used to select the portion of the cine may include an input from a trackball, an input from a mouse or an input from a touchpad or a touch-sensitive display according to various embodiments.

According to an embodiment, the plurality of single trace curves may also be used as part of a user interface to select and view a particular cardiac image from the cine. For example, the user may position an indicator (not shown) or select a location along the plurality of single trace curves 304 to display the cardiac image from the cine that corresponds to the location selected on the plurality of single trace curves 304. For example, the user may select with a cursor a position along the plurality of single trace curves 304 and the processor 116 may display the corresponding cardiac image that was acquired from the time represented at the selected location along the plurality of single trace curves 304.

Figure 4:
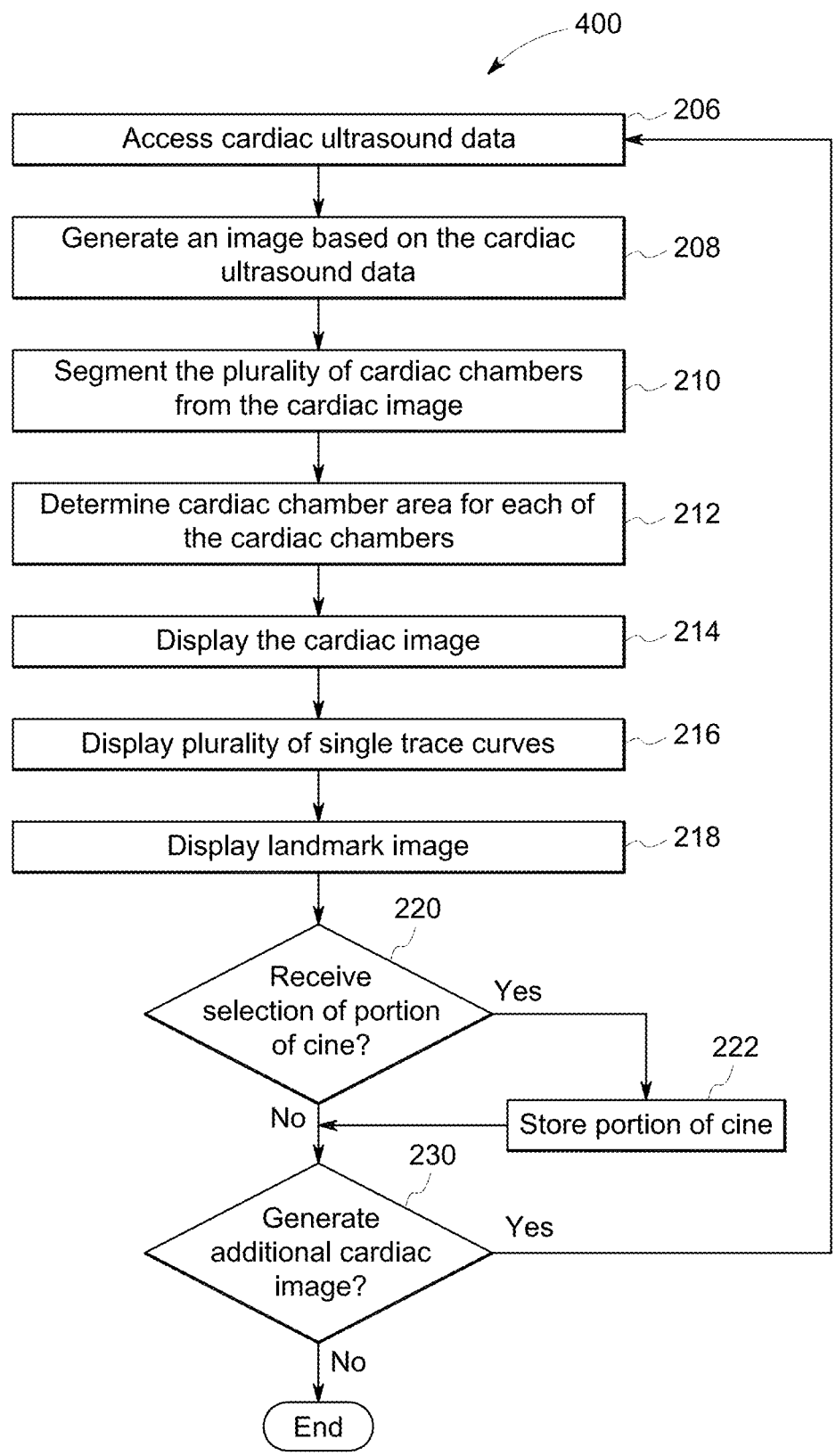
FIG. 4 shows a flow chart of a method according to an embodiment.

The method 400 is shown in FIG. 4 and will be described with respect to FIG. 1 and FIG. 5. Steps 206, 208, 210, 212, 214, 216, 220, 222, and 230 are the same as those that were previously described with respect to the method 200. Steps 206, 208, 210, 212, 214, 216, 220, 222, and 230 will not be described again with respect to the method 400. Compared to the method 200, the method 400, additionally includes new step 218. At step 218, the method 400 displays a landmark image. The method 400 will be described with respect to FIG. 5.

Figure 5:
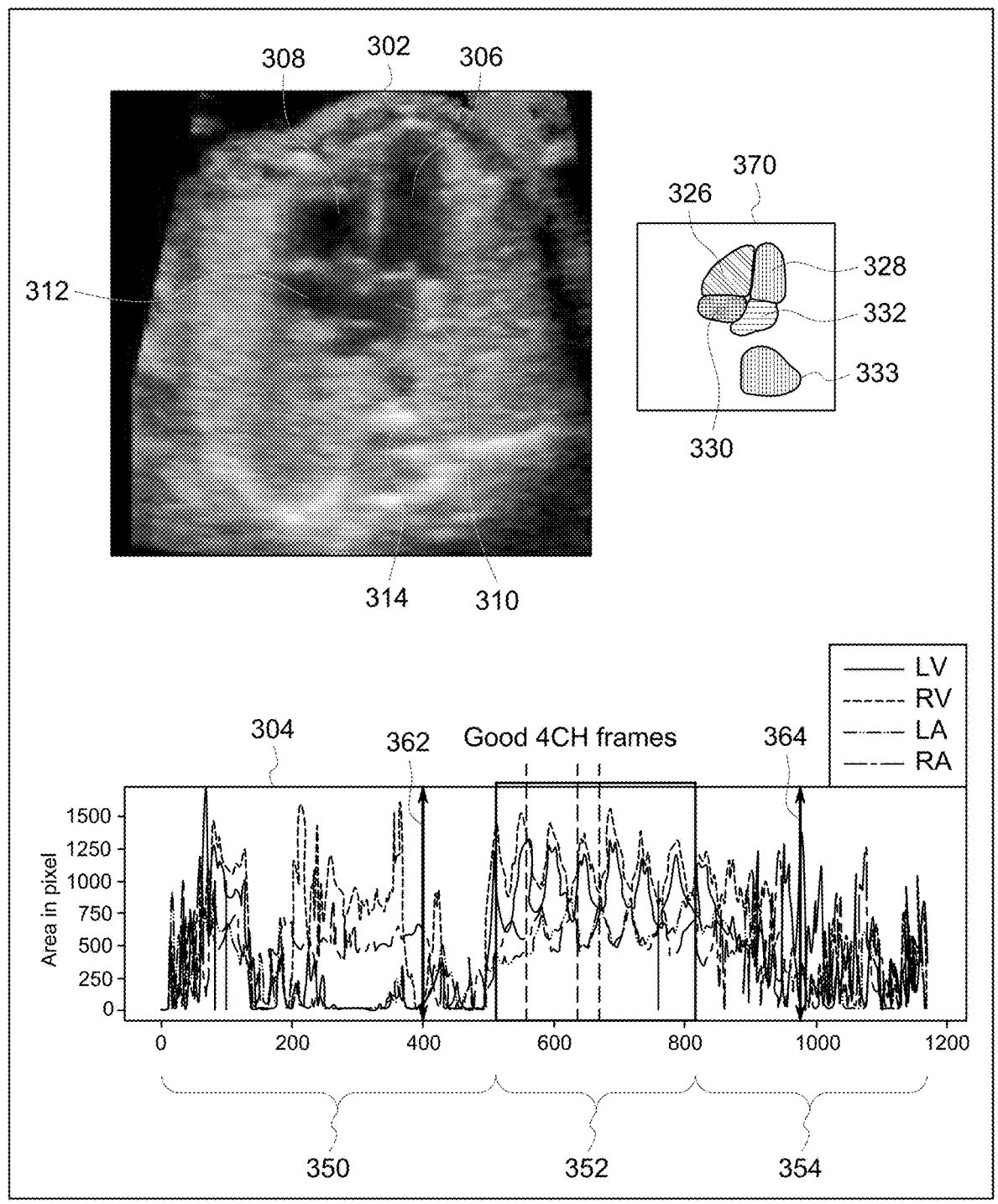
FIG. 5 shows a cardiac image, a plurality of single trace curves, and a landmark image according to an embodiment.

FIG. 5 shows the cardiac image 302, the plurality of single trace curves 304, and a landmark image 370 according to an embodiment. Both the cardiac image 302 and the plurality of single trace curves 304 were previously described with respect to FIG. 3 and the method 200 and will not be described again with respect to FIG. 5.

The landmark image 370 is a schematic representation of the plurality of cardiac chambers segmented from the cardiac image 302 displayed at step 214. The landmark image 370 shown in FIG. 5 is an example of a landmark image according to an embodiment. The landmark image 370 includes a schematic representation of the right ventricle 326, a schematic representation of the left ventricle 328, a schematic representation of the right atrium 330, and a schematic representation of the left atrium 332. The processor 116 may be configured to represent each of the plurality of structures in the landmark image 370 in a different color. For example, the processor 116 may represent the schematic representation of the right ventricle 326 in a first color, the schematic representation of the left ventricle 328 in a second color, the schematic representation of the right atrium 330 in a third color, and the schematic representation of the left atrium 332 in a fourth color. The processor 116 is configured to display the landmark image 370 on the display device 118 at the same time as the cardiac image 302 and the plurality of single trace curves 304. The landmark image 370 may include schematic representations of other structures according to various embodiments. For example, the landmark image 370 shown in FIG. 5 includes a schematic representation of the spine 333.

According to an embodiment, the processor 116 may obtain a mask of the plurality of structures that was segmented at step 210. For instance, processor 116 may generate a separate mask for each of the plurality of structures or the processor 116 may generate one mask for all of the plurality of structures. For example, the mask may define the locations of the left ventricle 306, the right ventricle 308, the left atrium 310, and the right atrium 312. According to various embodiments, the mask generated by the processor 116 may be a binary mask. At step 216, displaying the landmark image may include displaying a representation of the mask on the display device 118 at the same time as the cardiac image 302. According to other embodiments, the processor 116 may be configured to generate a different landmark image. For example, the processor 116 may create a landmark image that shows an outline or contour to schematically represent each of the plurality of structures segmented from the image. The landmark image 304 schematically represents the plurality of structures in the same relative positions and orientations as they are in the image displayed at step 214. It can take a relatively experienced clinician to quickly identify each of the plurality of structures in the cardiac image 302. Showing a schematic representation of the plurality of structures, such as in the landmark image 370, allows the clinician to quickly and easily determine if the current cardiac image 302 includes the plurality of structures in the correct orientation for the desired cardiac view, especially when viewed in combination with the plurality of single trace curves 304.

If, at step 230, it is desired to generate an additional image, the method 200 returns to step 206, where the processor 116 repeats steps 206, 208, 210, 212, 214, 216, 218, 220, and 230 with a different frame of the cardiac ultrasound data. The different frame of cardiac data may be either newly acquired as part of a real-time acquisition or it may be accessed from the memory 120. Each iteration through steps 206, 208, 210, 212, 214, 216, 218, 220, and 230 results in the display of an updated cardiac image at step 214 (based on an updated frame of cardiac ultrasound data), the display of a updated landmark image based on the segmentation of the plurality of structures from the updated cardiac image, and the display of an updated plurality of single trace curves. The processor 116 may be configured to repeat steps 206, 208, 210, 212, 214, 216, 218, 220, and 230 of the method 400 in real-time as cardiac ultrasound data is being acquired with the ultrasound probe 106. For example, the processor may, at step 230, return to step 206 if the ultrasound probe 106 has acquired an updated frame of cardiac ultrasound data. According to other embodiments, the processor 116 may iteratively cycle through steps 206, 208, 210, 212, 214, 216, 218, 220, and 230 of the method 400 using cardiac ultrasound data that was acquired and stored during a previous scanning session. For example, the processor 116 may access previously acquired cardiac ultrasound data from either the memory 120 of the ultrasound imaging system or from a remote memory device. According to an embodiment, the processor 116 may access previously acquired cardiac ultrasound data via a server and a remote memory or data storage device. The landmark image 370 is synchronized with the cardiac image 302. This means that the schematic representation of the plurality of structures in the landmark image 370 is based on the cardiac image 302 currently being displayed on the display device. The landmark image 370 is updated at the same refresh rate as the cardiac image 302 that is displayed as part of a cine on the display device 118. In the case of a live acquisition, where the cardiac image 302 is generated in real-time as additional frames of cardiac ultrasound data are acquired, the landmark image 370 provides a schematic representation of the plurality of structures included in the most recently acquired cardiac image 302, i.e., the cardiac image 302 that is currently being displayed on the display device 118. According to embodiments where the clinician is acquiring live ultrasound data, the clinician may make adjustments to the position and/or the orientation of the ultrasound probe 106 during the process of iteratively repeating steps 206, 208, 210, 212, 214, 216, 218, 220, and 230 of the method 200. Each time the method repeats steps 206, 208, 210, 212, 214, 216, 218, 220, and 230, the cardiac image 302 displayed on the display device 118 and the landmark image 304 displayed on the display device 118 will represent data acquired from the most-recent position and orientation of the ultrasound probe 106. An advantage of the landmark image 304 is that it helps the clinician to determine if the desired cardiac view has been acquired. The 4-chamber view, for example, should include all four cardiac chambers, the left ventricle should show the apex of the heart, and the 4-chamber view should include the tricuspid valve and the mitral valve. Displaying a landmark image, such as the landmark image 370, that is synchronized with the cine provides the clinician with real time feedback that is easy to interpret regarding the acquisition quality of the currently displayed cardiac image with respect to the desired cardiac view. If the clinician is acquiring data from a plane that is not in the correct location for the desired view, the clinician can easily see that the plurality of cardiac chambers (representing landmarks) shown in the landmark image are not in the right relative locations for the desired 4-chamber view. According to some embodiments, the processor 116 may also display a target landmark image which would show the relative orientations for the plurality of structures for the landmark image according to an example with a high acquisition quality. The user may then compare the landmark image to the target landmark image. This may help a less-experience clinician identify the desired 4-chamber view if the less-experienced clinician is not as familiar with expected relative orientations of the plurality of structures that would be represented in the 4-chamber view.

Method 400, shown in FIG. 4, is described below with regard to the ultrasound imaging system 100 and components depicted in FIG. 1, though it should be appreciated that method 400 may be implemented with other ultrasound systems and components without departing from the scope of the present disclosure. In some embodiments, method 400 may be implemented as executable instructions in any appropriate combination of the ultrasound imaging system 100, an edge device (e.g., an external computing device) connected to the ultrasound imaging system 100, a cloud in communication with the imaging system, and so on. As one example, method 400 may be implemented in non-transitory memory of a computing device, such as the processor 116 of the ultrasound imaging system 100 in FIG. 1. The method 400 includes many steps that are the same or substantially the same as those described with respect to the method 200. Steps that are substantially the same as steps that were previously described with respect to the method 200 will not be described in detail with respect to the method 400.

The methods 200 and 400 advantageously provide the user with qualitative feedback regarding an acquisition quality of the plurality of cardiac images in the cine. The user may use the qualitative information in the landmark image and/or the plurality of single trace curves in order to quickly and easily identify a portion of a previously acquired cardiac data represents a 4-chamber view. The user may also use the methods 200 or 400 when the cine represents real-time cardiac ultrasound data being acquired in real-time. For example, the user may, based on feedback from the landmark image and/or the plurality of single trace curves adjust the position and/or orientation of the ultrasound probe until the current cardiac image in the cine represent the desired cardiac view.

According to various embodiments, the user may use the landmark image 370 in order to identify when the plurality of structures in the landmark image are arranged in the relative positions that are associated with the desired view. The landmark image 370 may, for instance, only include the plurality of structures that were segmented by the processor 116. As such, the landmark image helps the user to more quickly determine, based on the plurality of structures representing landmarks for the desired cardiac view, the portion of the cardiac ultrasound data that was acquired with the ultrasound probe in the appropriate position and orientation.

According to various embodiments, the user may use the plurality of single trace curves 304 either in addition to the landmark image 370 or instead of the landmark image 370 in order to quickly and easily determine qualitative information about the acquisition quality with respect to the desired 4-chamber view. For example, when the desired cardiac view is the 4-chamber view and the cardiac chamber areas represented in the plurality of single trace curves are expected to change with a generally synchronized periodicity. In contrast, when the cardiac image is not acquired from the correct plane, the plurality of single trace curves will not display the same synchronized periodicity. The user may, for example, adjust the position and orientation of the ultrasound probe 106 in real-time until the plurality of single trace curves based on the cardiac image displayed in the cine exhibit synchronized periodicity. The user is looking for an ultrasound probe position and orientation where the motion of the four cardiac chambers is rhythmic and stable as determined by one or both of the landmark image 370 and the plurality of single trace curves 304. According to some embodiments, the processor 116 may be configured to automatically save the best one or more cycles of the cardiac ultrasound data in the cine as determined based on the metrics in the plurality of single trace curves and/or the plurality of structures segmented for the landmark image.

According to an embodiment, the plurality of single trace curves may also be used as part of a user interface to select and view a particular cardiac image from the cine and a corresponding landmark view. For example, the user may position an indicator (not shown) or select a location along the plurality of single trace curves 304 to display the cardiac image from the cine that corresponds to the location selected on the plurality of single trace curves 304 and to display a corresponding landmark image. The landmark image may, according to an embodiment, always correspond to the currently displayed cardiac image. For example, the user may select with a cursor a position along the plurality of single trace curves 304 and the processor 116 may display the corresponding cardiac image and the corresponding landmark image that was acquired from the time represented at the selected location along the plurality of single trace curves 304.

Figure 6:
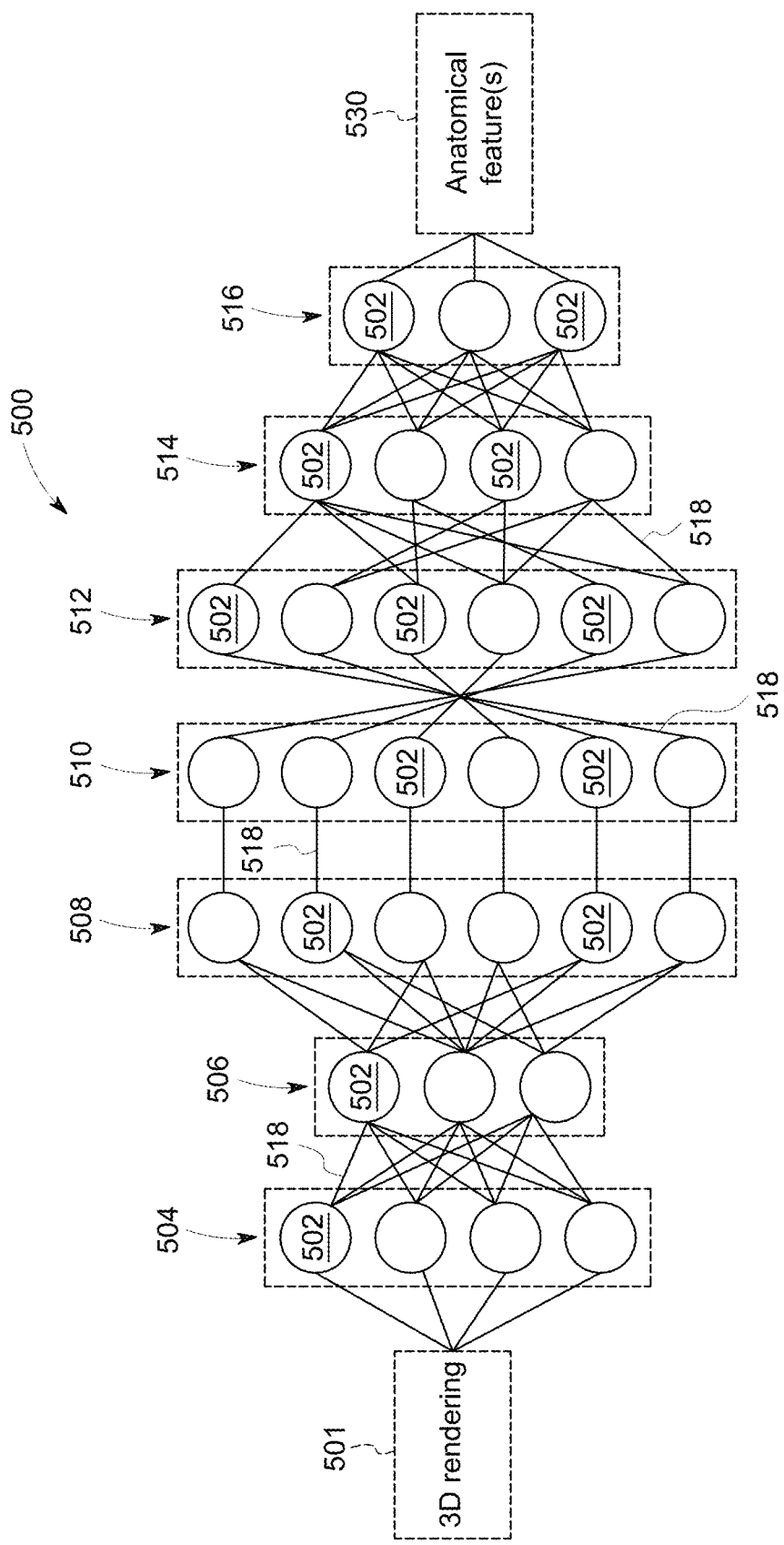
FIG. 6 shows a schematic diagram of a neural network according to an embodiment.
Figure 7:
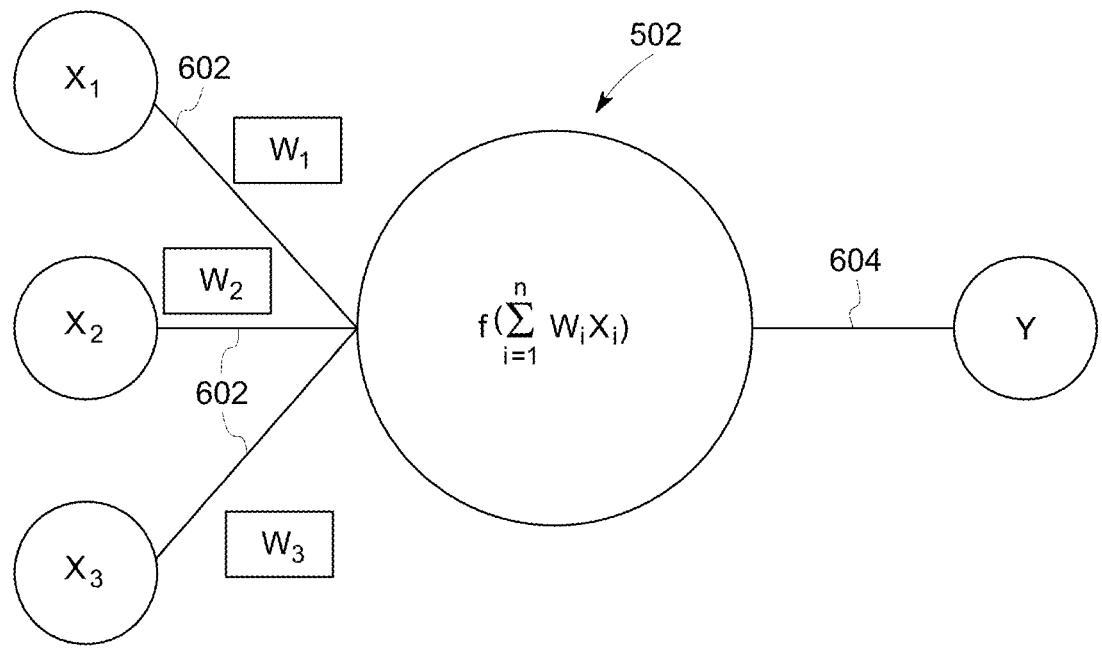
FIG. 7 shows input and output connections for a neuron according to an embodiment.

Referring now to FIGS. 6 and 7, an exemplary neural network for identifying and segmenting the plurality of structures from the cardiac image in accordance with an exemplary embodiment is shown. In some examples, the neural network may be trained with a training set of cardiac images.

FIG. 6 depicts a schematic diagram of a neural network 500 having one or more nodes/neurons 502 which, in some embodiments, may be disposed into one or more layers 504, 506, 508, 510, 512, 514, and 516. Neural network 500 may be a deep neural network. As used herein with respect to neurons, the term "layer" refers to a collection of simulated neurons that have inputs and/or outputs connected in similar fashion to other collections of simulated neurons. Accordingly, as shown in FIG. 6, neurons 502 may be connected to each other via one or more connections 518 such that data may propagate from an input layer 504, through one or more intermediate layers 506, 508, 510, 512, and 514, to an output layer 516.

FIG. 7 shows input and output connections for a neuron in accordance with an exemplary embodiment. As shown in FIG. 7, connections (e.g., 518) of an individual neuron 502 may include one or more input connections 602 and one or more output connections 604. Each input connection 602 of neuron 502 may be an output connection of a preceding neuron, and each output connection 604 of neuron 502 may be an input connection of one or more subsequent neurons. While FIG. 9 depicts neuron 502 as having a single output connection 604, it should be understood that neurons may have multiple output connections that send/transmit/pass the same value. In some embodiments, neurons 502 may be data constructs (e.g., structures, instantiated class objects, matrices, etc.), and input connections may be received by neuron 502 as weighted numerical values (e.g., floating point or integer values). For example, as further shown in FIG. 9, input connections $X_1$, $X_2$, and $X_3$ may be weighted by weights $W_1$, $W_2$, and $W_3$, respectively, summed, and sent/transmitted/passed as output connection Y. As will be appreciated, the processing of an individual neuron 502 may be represented generally by the equation:

$$Y = f\left(\sum_{i=1}^{n} W_i X_i\right)$$

where n is the total number of input connections 602 to neuron 502. In one embodiment, the value of Y may be based at least in part on whether the summation of $W_i X_i$ exceeds a threshold. For example, Y may have a value of zero (0) if the summation of the weighted inputs fails to exceed a desired threshold.

As will be further understood from FIGS. 6 and 7, input connections 602 of neurons 502 in input layer 504 may be mapped to an input 501, while output connections 604 of neurons 502 in output layer 516 may be mapped to an output 530. As used herein, "mapping" a given input connection 602 to input 501 refers to the manner by which input 501 affects/dictates the value said input connection 602. Similarly, as also used herein, "mapping" a given output connection 604 to output 530 refers to the manner by which the value of said output connection 604 affects/dictates output 530.

Accordingly, in some embodiments, the acquired/obtained input 501 is passed/fed to input layer 504 of neural network 500 and propagated through layers 504, 506, 508, 510, 512, 514, and 516 such that mapped output connections 604 of output layer 516 generate/correspond to output 530. As shown, input 501 may include a cardiac image. The cardiac image may depict a one or more structures that are identifiable by the neural network 500. Further, output 530 may include locations and contours for the one or more structures that are identified by the neural network 500.

Neural network 500 may be trained using a plurality of training datasets. Each training dataset may include cardiac images that are, for example, annotated. Based on the training datasets, the neural network 500 may learn to identify a plurality of structures from the cardiac images. The machine learning, or deep learning, therein (due to, for example, identifiable trends in placement, size, etc. of anatomical features) may cause weights (e.g., $W_1$, $W_2$, and/or $W_3$) to change, input/output connections to change, or other adjustments to neural network 500. Further, as additional training datasets are employed, the machine learning may continue to adjust various parameters of the neural network 500 in response. As such, a sensitivity of the neural network 500 may be periodically increased, resulting in a greater accuracy of anatomical feature identification.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of ultrasound imaging comprising:
accessing with a processor cardiac ultrasound data;
generating a cine based on the cardiac ultrasound data, wherein the cine includes a plurality of cardiac images acquired over a plurality of cardiac cycles;
automatically segmenting a plurality of cardiac chambers from each of the plurality of cardiac images;
automatically determining a cardiac chamber area for each of the plurality of cardiac chambers segmented from each of the plurality of cardiac images;
displaying the cine on a display device;
displaying a plurality of single trace curves on the display device at the same time as the cine to provide feedback regarding an acquisition quality of the cine, wherein each of the plurality of single trace curves represents the cardiac chamber area for a different one of the plurality of cardiac chambers over the plurality of cardiac cycles;
receiving a selection of a portion of the cine based on the information displayed in the plurality of single trace curves; and
saving the portion of the cine in a memory as a 4-chamber view based on the selection.

2. The method of claim 1, wherein the portion of the cine represents at least one complete cardiac cycle and comprises a second plurality of cardiac images, wherein the second plurality of cardiac images is a subset of the plurality of cardiac images.

3. The method of claim 2, wherein each of the second plurality of cardiac images exceeds an acquisition quality threshold determined based on the information displayed in the plurality of single trace curves.

4. The method of claim 1, wherein the feedback regarding the acquisition quality of the cine comprises an amount of synchronization between the plurality of single trace curves.

5. The method of claim 1, wherein receiving the selection of the portion of the cine comprises receiving an input entered through a user interface.

6. The method of claim 5, further comprising displaying a graphical indicator on the plurality of single trace curves to indicate where the acquisition quality of the cine exceeds an acquisition quality threshold.

7. The method of claim 1, wherein receiving the selection comprises automatically receiving the selection from a processor based on an analysis of the information displayed in the plurality of single trace curves to identify the portion of the cine when the acquisition quality exceeds an acquisition quality threshold.

8. The method of claim 7, wherein said automatically receiving the selection from the processor comprises using a neural network to identify the portion of the cine.

9. The method of claim 7, wherein the analysis of the information displayed in the plurality of single trace curves comprises determining an amount of synchronization in the information displayed as the plurality of single trace curves.

10. The method of claim 1, further comprising displaying a landmark image on the display device at the same time as the cine and the plurality of single trace curves, wherein the landmark image comprises a schematic representation of the plurality of cardiac chambers currently displayed in the cine.

11. The method of claim 10, wherein each of the plurality of structures is represented in a different color in the landmark image.

12. An ultrasound imaging system, comprising:
an ultrasound probe;
a user interface;
a display device; and
a processor in electronic communication with the ultrasound probe, the user interface and the display device, wherein the processor is configured to:
control the ultrasound probe to acquire cardiac ultrasound data;
generate a cine based on the cardiac ultrasound data, wherein the cine includes a plurality of cardiac images;
automatically segment a plurality of cardiac chambers from each of the plurality of cardiac images;
automatically determine a cardiac chamber area for each of the plurality of cardiac chambers segmented from each of the plurality of cardiac images;
display the cine on the display device; and
display a plurality of single trace curves on the display device at the same time as the cine to provide feedback regarding an acquisition quality of the cine, wherein each of the plurality of single trace curves represents the cardiac chamber area for a different one of the plurality of cardiac chambers over the plurality of cardiac cycles;
receive a selection of a portion of the cine based on the information displayed in the plurality of single trace curves; and
save the portion of the cine in the memory as a 4-chamber view.

13. The ultrasound system of claim 12, wherein the portion of the cine represents at least one complete cardiac cycle and comprises a second plurality of cardiac images, wherein the second plurality of cardiac images is a subset of the plurality of cardiac images.

14. The ultrasound system of claim 13, wherein each of the second plurality of cardiac images exceeds an acquisition quality threshold determined based on the information displayed in the plurality of single trace curves.

15. The ultrasound system of claim 12, wherein the feedback regarding an acquisition quality comprises an amount of synchronization.

16. The ultrasound system of claim 12, wherein the processor is configured to receive the selection of the portion of the cine based on an input entered through the user interface.

17. The ultrasound system of claim 12, wherein the processor is further configured to display a graphical indicator on the plurality of single trace curves to indicate where the acquisition quality of the cine exceeds an acquisition quality threshold.

18. The ultrasound system of claim 12, wherein the processor is configured to identify the portion of the cine based on an amount of synchronization in the information displayed as the plurality of single trace curves.

19. The ultrasound system of claim 18, wherein the processor is configured to receive the selection of the portion of the cine based on an output from a neural network to identify the portion of the cine.

20. The ultrasound system of claim 12, wherein the processor is further configured to display a landmark image on the display device at the same time as the cardiac image and the plurality of single trace curves.

* * * * *